United States Patent [19]

Kronick

[11] 4,375,407
[45] Mar. 1, 1983

[54] HIGH GRADIENT MAGNETIC SEPARATION DEVICE

[75] Inventor: Paul L. Kronick, Haverford, Pa.

[73] Assignee: The Franklin Institute, Philadelphia, Pa.

[21] Appl. No.: 275,905

[22] Filed: Jun. 22, 1981

[51] Int. Cl.³ .............................................. B03C 1/02
[52] U.S. Cl. ...................................... 209/8; 209/214; 209/223 R; 209/232
[58] Field of Search .................. 209/214, 223 R, 232, 209/39, 8, 4, 213; 210/222, 223

[56] References Cited

U.S. PATENT DOCUMENTS

| | | | |
|---|---|---|---|
| 2,979,202 | 4/1961 | Orbeliani | 210/222 X |
| 3,024,392 | 3/1962 | Baermann | 210/222 X |
| 3,136,720 | 6/1964 | Baermann | 210/222 |
| 3,279,602 | 10/1966 | Kottenstette et al. | 209/223 R X |
| 3,627,678 | 12/1971 | Marston et al. | 210/222 X |
| 3,865,617 | 2/1975 | Shimizu | 117/132 |
| 3,970,518 | 7/1976 | Giaever | 209/8 X |
| 4,047,814 | 9/1977 | Westcott | 209/214 X |
| 4,070,246 | 1/1978 | Kennedy et al. | 195/103.5 |
| 4,078,998 | 3/1978 | Oder et al. | 210/222 X |
| 4,157,323 | 6/1979 | Yen et al. | 260/29.7 |
| 4,219,411 | 8/1980 | Yen et al. | 209/223 R X |

OTHER PUBLICATIONS

Science, vol. 200, pp. 1074-1076, Jun. 2, 1978.

*Primary Examiner*—Ralph J. Hill
*Attorney, Agent, or Firm*—Dann, Dorfman, Herrell and Skillman

[57] ABSTRACT

An improved high gradient magnetic separation device wherein field gradients are produced by applying a relatively uniform magnetic field to a matrix of filamentary ferromagnetic material contained in a separation chamber, the improvement comprising providing the filamentary material with a coating of a hydrogel polymer. The improved device is particularly useful for the separation of biological entities, such as cells, proteins, organelles, enzymes, and the like for mixtures containing same.

7 Claims, 3 Drawing Figures

HIGH GRADIENT MAGNETIC SEPARATION DEVICE

DESCRIPTION

BACKGROUND OF THE INVENTION

The present invention relates to high gradient magnetic separation (HGMS) devices, and in particular, to an improved HGMS device useful for the isolation of biological entities.

Numerous magnetic separation techniques have been developed over the years in connection with efforts to improve mineral processing. More recently, magnetic separation techniques have been used effectively for locating and isolating biological entities, such as cells, proteins, organelles, enzymes, and the like. These techniques typically involve introducing magnetic particles into a liquid sample containing a mixture of the biological entity to be isolated with various other biological entities. In most instances, the magnetic particles are coated with a material having an affinity for the target biological entity thus causing the magnetic particles to become attached to the target biological entity in preference to the other entities admixed therewith. Subsequently, a magnetic field provided by an electromagnet, for example, is applied to the liquid sample, thereby immobilizing the magnetic particles carrying the target biological entities against the walls of the sample container. The target biological entities are then separated from the liquid sample. For specific applications of such techniques, see: Giaver, U.S. Pat. No. 4,018,886; P. Dunnill et al, 16 Biotechnology and Bioengineering 987 (1974); R. Molday et al, 268 Nature 437 (1977); and P. Kronick et al, 200 Science 1074 (1978).

For certain applications these techniques have not been completely satisfactory because the population of biological entities retained by the magnet also contains other undesired substances as well. Removal of the undesired substances often requires repeated passing of the mixture through the separation device.

Advances in the art of magnetic separation have led to the development of HGMS devices in which it is possible to separate very weakly magnetic materials of small particle size. These devices are well known to those skilled in the art, and typically comprise a separation vessel, e.g., a canister, containing a ferromagnetic material, such as steel wool, through which the materials to be separated are passed. High field gradients result from applying a relatively uniform background magnetic field to the ferromagnetic filamentary material. The strong magnetic forces produced by the high field gradients at the edges of the filaments are effective in immobilizing particles of even weakly magnetic material.

Although HGMS devices of the type described above have been employed with varying degrees of success in chemical processing, pollution control, and the beneficiation of non-ferrous low grade ores, such devices have not produced completely satisfactory results when applied to the separation of biological entities. The reason is that both the biological entities sought to be isolated and other undesired entities often adhere to the metal filaments even after the applied magnetic field is reduced to zero. In certain instances, contact between the metal filaments and the biological entities has actually damaged the latter.

SUMMARY OF THE INVENTION

In one aspect, the present invention provides an improved HGMS device of the type which employs a matrix of ferromagnetic filamentary material as the magnetic gradient intensifier. In general, HGMS devices comprise a chamber containing a matrix of ferromagnetic filamentary material and having an inlet and a discharge port through which the materials to be separated are passed, and magnetic means disposed in association with the ferromagnetic filamentary material for applying a magnetic field thereto. In accordance with the present invention the matrix of ferromagnetic filamentary material is provided with a coating of a hydrogel polymer to facilitate biological separations. The device is capable of effectively separating particular biological entities from a mixture containing same, and prevents the separated biological entities from adhering to or being damaged by the filamentary material.

In another aspect, this invention provides an efficient and effective method for isolating particular biological entities from a mixture containing same. This is accomplished by contacting the mixture with a conjugate comprising a magnetic particle and a substance having a high degree of affinity for the target biological entity, thereby forming a complex of the target biological entity and the conjugate, and passing the mixture through the improved HGMS device of the present invention. The magnetized polymer-coated ferromagnetic filamentary matrix attracts and holds the complex as the remainder of the mixture passes out of the device.

Other aspects and advantage of the invention will be apparent to those skilled in the art from the following detailed description thereof read in conjunction with the accompanying drawing, in which.

DESCRIPTION OF THE PREFERRED EMBODIMENT

Figure 1:
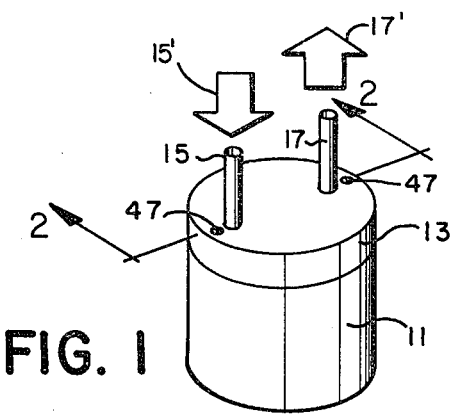
FIG. 1 is a perspective view of an improved HGMS device in accordance with the present invention.

Referring more specifically to the drawing, FIG. 1 shows the exterior of the improved HGMS device of the present invention which comprises a base member 11 and a cover-plate 13 provided with inlet means 15 and outlet means 17, for introducing and withdrawing a test specimen from the HGMS device, as indicated by arrows 15' and 17'.

Base member 11 is preferably of cylindrical configuration, having an annular channel 21 for receiving a coil 23 formed by winding an electrically conductive wire in a more or less helical configuration. Channel 21 divides base member 11 into two portions, an outer portion 27 and an inner portion 29. Coil 23 is connected to a D.C. source (not shown) by leads 25, 25'. Base member 11 thus functions as an electromagnet with outer portions 27 and inner portion 29 together serving as the core of the electromagnet. A ring of insulation material 31, such as silicone rubber is provided on the upper surface of the coil for protection.

The base member should be made of a material having relatively high magnetic permeability. Ferromagnetic materials are preferred, since the use of a ferromagnetic core significantly enhances the strength of the electromagnet. Suitable ferromagnetic materials include iron, cobalt, nickel, manganese and alloys thereof.

Resting on the upper surface of the core 29 of the electromagnet is the magnetic gradient intensifier 33, which comprises a substrate 35 on which is provided a matrix of polymer-coated, ferromagnetic filamentary material 37, e.g. steel wire. The magnetic gradient intensifier may be prepared simply by wrapping the filamentary material around the substrate from one end to the other. Various materials may be used as the substrate, so long as they are non-magnetic and inert to the biological substances being separated using this device. Satisfactory results have been obtained using a glass microscope cover slip as the substrate. To increase the capacity of the device, the substrate may be omitted altogether, in favor of a magnetic gradient intensifier in the form of a bat or wad of polymer-coated steel wool, for example.

Figure 2:
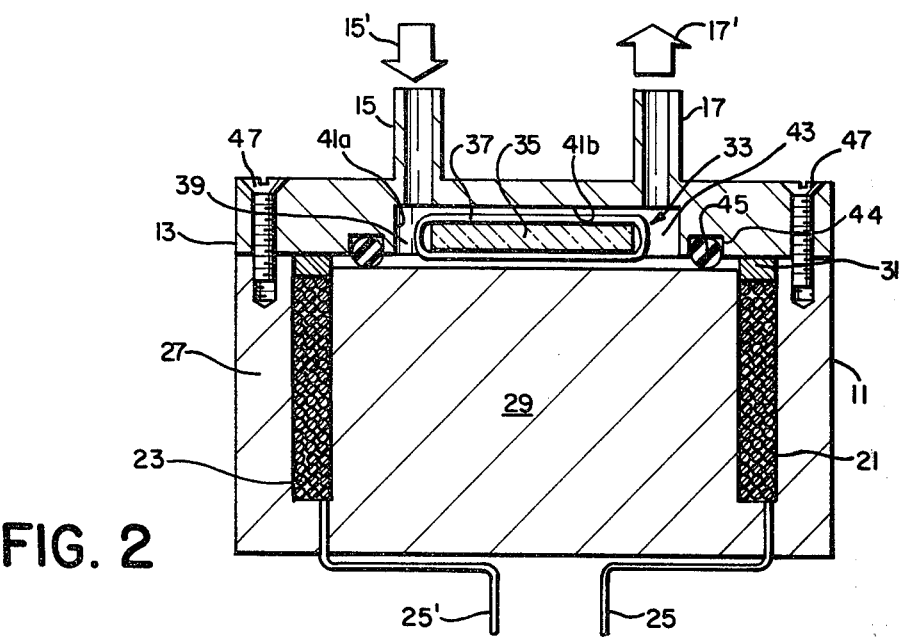
FIG. 2 is a sectional view taken on line 2—2 of FIG. 1 showing the internal arrangement of the various parts of the HGMS devices.
Figure 3:
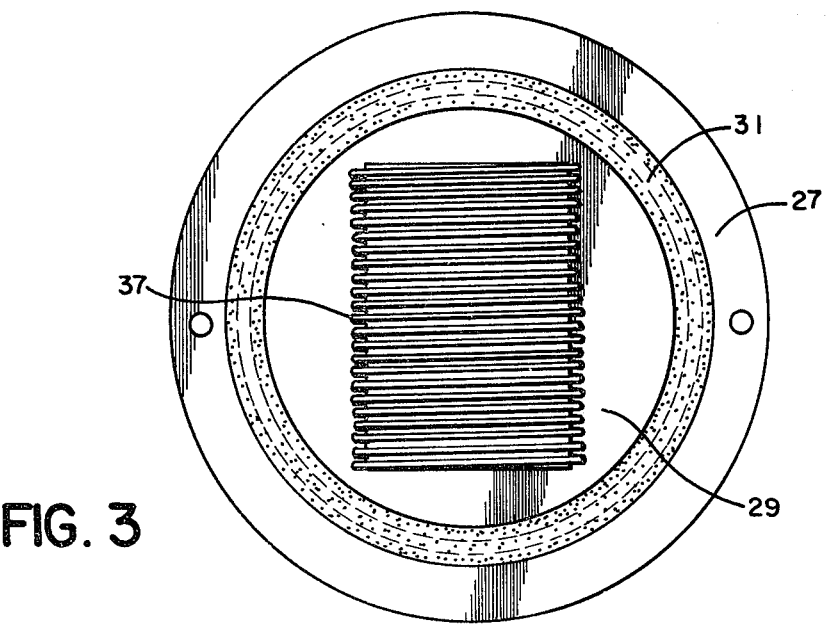
FIG. 3 is a plan view of the HGMS device of FIG. 1 with the cover plate removed.

The magnetic gradient intensifier is disposed in a separation chamber 39 defined by the upper surface of the core 29 of the electro-magnet and the surfaces 41a, 41b, of a circular cavity 43 centrally located in the underside of coverplate 13. As shown in FIG. 2, inlet 15 and outlet 17 for the test specimens are in communication with separation chamber 39. The underside of cover plate 13 is also provided with an annular notch 44 of slightly greater diameter than the cavity 43, and arranged concentrically therewith. Seated in the notch 44 is a sealing ring 45 for preventing leakage of the test specimen from the separation chamber onto coil 23. Cover plate 13 is secured to base member 11 by suitable fastening means, such as screws 47. In FIG. 3, which shows the top of the HGMS device with the cover plate removed, there is seen the magnetic gradient intensifier 33 centrally disposed on the core 29 of the electro-magnet. Also shown in FIG. 3 is the insulation ring 31 covering the coil of the electro-magnet and the top of side wall 27.

In accordance with the present invention, filamentary material 37 comprising the magnetic gradient intensifier has a coating of a hydrogel polymer provided thereon. As used herein, the expression "hydrogel polymer" is intended to signify a polymer which imbibes or absorbs water to the extent of at least 30% of the weight of the polymer. Representative of the polymers having this characteristic are those produced from hydrophilic acrylic-type monomers, particularly those bearing functional groups, such as hydroxyl, carboxyl, amino, amido, isocyanate or isothiocyanate radicals. Specific examples of the acrylic-type monomers which may be employed in accordance with the present invention include acrylamide, hydroxyethyl methacrylate, N, N'-methylene-bis-acrylamide and methacrylic acid. In the presence of a small amount of polyfunctional cross-linking agent, these monomers polymerize to hydrogels, which do not normally interact with biological entities. The use of polymers which do not imbibe or absorb water must be avoided, since various types of biological entities, e.g., white blood cells, have a tendency to adhere to such polymers.

In carrying out the method of the present invention, magnetic particles which have been conjugated with a substance having a high degree of affinity for the biological entity to be isolated are introduced into a liquid test specimen containing the target biological entity. The magnetic particles become attached preferentially to the target biological entity, thus forming a complex. The test specimen is then introduced into the HGMS device, and as it passes through chamber 39, the complexes are immobilized on the ferromagnetic filamentary material 37 which has a relatively uniform magnetic field applied thereto by the electro-magnet. Although the application of a uniform magnetic field is desirable for optimum operating efficiency, separations may be effected using a non-uniform magnetic field. After the liquid specimen has been withdrawn from separation chamber 39 through outlet 17, the magnetic particles with the target biological entities attached thereto are easily washed out when the applied magnetic field is reduced to zero.

Examples of substances with which the magnetic particles may be conjugated in order to effect a separation of a particular biological entity from a mixture containing same include various proteins, antibodies, immunoglobulins, lectins, enzymes, hormones, toxins, or various natural and synthetic drugs. Conjugation can be achieved by various means well-known to those skilled in the art, e.g., by covalent bonding to a polymer coating on the magnetic particles, or by ionic or hydrogen bonding.

Polymer-coated magnetic particles which are useful in the separation of biological entities and well suited for use in connection with the improved HGMS device of the present invention are those disclosed in my co-pending U.S. application Ser. No. 44,099 filed May 31, 1979, the complete disclosure of which is incorporated herein by reference.

The polymer coating of the magnetic gradient intensifier may be effectively applied by a redox polymerization process wherein the ferromagnetic filamentary material itself serves as the source of the reducing agent in the redox activation system. For example, the preparation of a polymer-coated steel wire by a free radical-initiated redox polymerization proceeds by a mechanism in which ferrous ion dissolved from the steel wire reacts with an oxidizing agent to initiate the polymerization reaction in the vicinity of the wire. Thus, a polymer coating is formed directly on the surface of the wire. Although other methods well known to those skilled in the art for applying a polymer coating to a metal substrate may also be used, the redox method is preferred because it results in a thin coating, on the order of one-half mil or less, of substantially uniform thickness on the filamentary material and obviates post-polymerization processing to obtain discrete filaments, such as would likely be required if mass polymerization techniques were employed.

A variety of ferromagnetic substances may be employed as the filamentary matrix, e.g., iron, cobalt, nickel, manganese or alloys thereof. The diameter of the filamentary material making up the magnetic gradient intensifier will depend upon the particular biological entities being separated, the optimum diameter being approximately three times the diameter of the biological entity. See: W. A. Oberteuffer, "Magnetic Separation, A Review of Principles, Devices and Applications", I.E.E.E. Transactions on Magnetics, Vol. MAG-10, No. 2, pp. 223–38 (1974). In the case of animal cells, for example, the filamentary diameter may vary between about 0.001 inch and about 0.01 inch.

The oxidizing agent of the redox system can be any of the peroxy compounds such as are used in conventional redox polymerization processes. Typical peroxy compounds include peroxides, such as benzoyl peroxide, caprylyl peroxide, perchlorobenzoyl peroxide, and lauroyl peroxide, hydroperoxides, such as cumene hydroperoxide, t-butyl hydroperoxide, and diisopropylbenzene hydroperoxide, and persulphates, such as ammonium persulphate.

Polymerization can be carried out conveniently under essentially normal or well-known conditions, i.e., under atmospheric pressure, at about room temperature, for instance 20° C. to 30° C. and for time periods sufficient to obtain the desired results. In certain instances, for example, when thermal dissociation of the peroxides is a problem, it may be desirable to carry out the polymerization at temperatures as low as 0° C. to 5° C., while other circumstances may require temperatures approaching 100° C. or other than atmospheric pressure.

The pH of the polymerization reaction mixture should preferably be about 1 to about 4. For best results, the pH should be selected to be as high as possible, consistent with a convenient rate of polymerization. If the pH is too low, an excess of ferrous ion will be produced forming radicals at a rapid rate and resulting in polymerization in the solution not adjacent to the wire. Also, the initiation rate of the polymerization reaction is excessive at low pH because of the high concentration of radicals, with the attendant formation of short chains not bound into the hydrogel by crosslinks. The optimum pH will depend on the specific type of ferromagnetic filamentary material used, and must be determined by experimentation. In general, it is preferred to employ an aqueous medium with appropriate dispersants, wetting agents, surfactants, etc., to dissolve, suspend or emulsify the particular monomer or monomers as well as the initiation ingredients, as is well known in the art.

Polymerization can also be carried out in a non-aqueous medium such as appropriate aliphatic or aromatic hydrocarbons, as well as alcohols, ethers, esters, amides nitriles and other functional dispersion media. Polymerization can also be carried out "neat", that is in the absence of a liquid or other reaction medium.

The amount of polymeric coating on the ferromagnetic filamentary material may vary within a rather broad range. In general, the coating on the filaments will correspond to at least 10% of their weight and up to about 100% of their weight and usually between 40% and 60% of their weight.

The strength of the applied magnetic field may vary in accordance with the flow rate of the liquid sample containing the biological entity to be isolated, up to the saturation field of the ferromagnetic wire. In any event, the force generated by the applied magnetic field must be larger than the hydrodynamic drag force which the flow of the liquid sample exerts on the immobilized magnetic particles. For example, when separating animal cells using the polymer-coated magnetic particles of my copending U.S. application Ser. No. 44,099, referred to previously, a linear flow rate of about 10 cm/min. may be employed with a magnetic field strength in the range between 5,000 Gauss and 10,000 Gauss.

Additional details concerning the manner in which the present invention may be carried out are set forth in the following examples.

EXAMPLE 1

A magnetic gradient intensifier was prepared from a 0.002-inch thick wire made from No. 401 stainless steel (magnetizable), which was wrapped as closely as possible around the short dimension of a glass plate 2 cm × 1 cm × 0.02 cm. This assembly was placed in a mixture of aqueous 10% acrylamide, 1% N, N'-methylene-bisacrylamide, and 0.5% ammonium peroxydisulfate, the latter being the oxidizing agent of the redox system. The pH of the mixture was 2. A low pH was used to insure the oxidation of the steel wire to generate ferrous ion. In 5 minutes, the wire was coated with attached polyacrylamide in the form of a soft but insoluble gel a few tenths of a millimeter thick.

EXAMPLE 2

One million ordinary HeLa cells, and one million cells from a cloned HeLa line which did not have free galactose residues on the cell surface (Line $R^R II$), and fluorescent magnetic microspheres in the form of polymer-coated magnetite particles (Wright Industries #4100) conjugated with the affinity ligand ricin were placed in a reservoir containing cell culture medium. The ricin binds the microspheres to galactose moities on the surfaces of the ordinary cells which bear this sugar residue, making these cells magnetic. The suspension of mixed cells was passed from the reservoir through the inlet of a HGMS device of the type shown in the accompanying drawing containing the magnetic gradient intensifier of Example 1 with the electo-magnet energized. Thereafter, the separation chamber was washed with medium. The cells which passed through the device were devoid of microspheres and were found to be resistant to the toxic effects of the ricin. The separation chamber of the HGMS device, which still contained cells bound to the polymer coated wire by their attached microspheres, was filled from the reservoir with culture medium. The electro-magnet was de-energized, and the contents of the separation chamber were then washed into culture flasks. These retained cells were almost exclusively cells that were complexed with ricin-microsphere conjugates.

EXAMPLE 3

Example 2 was repeated using the same magnetic gradient intensifier prepared in the same way, but having no polymer coating thereon. In this case, the cells which were eluted after the electro-magnet was de-energized were obviously damaged, appearing as fluorescent debris. When the filamentary material was removed from the HGMS device and examined under a microscope, it was observed that it was still covered with cells bearing microspheres, which could not be dislodged without damage.

EXAMPLE 4

The procedure of Example 2 was again performed, substituting an uncoated stainless steel bat in the HGMS device for the magnetic gradient intensifier of Example 1. In this case also the cells bearing microspheres, once having been attached to the stainless steel bat could not be removed after the magnetic field was terminated.

Although a particular embodiment of the present invention has been illustrated, the invention is susceptible of various modifications without departing from the spirit and scope thereof, as set forth in the appended claims.

I claim:

1. A high gradient magnetic separation device comprising a chamber having an inlet and a discharge port through which the materials to be separated are passed, said chamber containing a matrix of ferromagnetic filamentary material, and magnetic means disposed in association with said chamber for applying a magnetic field to said matrix of ferromagnetic filamentary material, wherein the improvement comprises providing said matrix of ferromagnetic filamentary material with a coating of a hydrogel polymer.

2. The device of claim 1 wherein the hydrogel polymer comprises an acrylic homopolymer or copolymer.

3. The device of claim 2 wherein the acrylic homopolymer or copolymer comprises monomers selected from the group consisting of acrylamide, hydroxyethethyl methacrylate, N, N'-methylene-bis-acrylamide and methacrylic acid.

4. The device of claim 3 wherein the hydrogel polymer is a homopolymer of acrylamide.

5. A method for separating a particular biological entity from a mixture of biological entities which comprise contacting the mixture with a conjugate comprising a magnetic particle and a substance having a high degree of affinity for the particular biological entity to be separated, thereby producing a complex of said particular biological entity with said conjugate, and passing the mixture through a high gradient magnetic separation device containing a matrix of ferromagnetic filamentary material having a magnetic field applied thereto, said filamentary material being provided with a hydrogel polymer coating, whereby the complex is attracted to the ferromagnetic filamentary material and held thereon as the remainder of the mixture passes out of the device.

6. The method of claim 5 including the additional step of reducing the magnetic field to zero.

7. The method of claim 6 including the additional step of washing the complex out of the high gradient magnetic separation device.

* * * * *